(12) United States Patent
Sturek et al.

(10) Patent No.: US 9,414,901 B2
(45) Date of Patent: Aug. 16, 2016

(54) DRUG-ELUTING STENTS FOR ADENOSINE RECEPTOR MODULATION

(75) Inventors: Michael Sturek, Zionsville, IN (US); Kinam Park, West Lafayette, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 1171 days.

(21) Appl. No.: 12/896,501

(22) Filed: Oct. 1, 2010

(65) Prior Publication Data

US 2011/0189255 A1 Aug. 4, 2011

Related U.S. Application Data

(60) Provisional application No. 61/247,731, filed on Oct. 1, 2009.

(51) Int. Cl.
| | |
|---|---|
| A61F 2/00 | (2006.01) |
| A61K 31/44 | (2006.01) |
| A61K 31/4545 | (2006.01) |
| A61K 31/519 | (2006.01) |
| A61K 31/52 | (2006.01) |
| A61K 31/522 | (2006.01) |
| A61K 31/7076 | (2006.01) |

(52) U.S. Cl.
CPC . *A61F 2/00* (2013.01); *A61K 31/44* (2013.01); *A61K 31/4545* (2013.01); *A61K 31/519* (2013.01); *A61K 31/52* (2013.01); *A61K 31/522* (2013.01); *A61K 31/7076* (2013.01)

(58) Field of Classification Search
CPC .... A61F 2/00; A61K 31/4545; A61K 31/519; A61K 31/52; A61K 31/522; A61K 31/7076; A61L 2300/432; A61L 27/54; A61L 31/10; A61L 31/16
See application file for complete search history.

(56) References Cited

U.S. PATENT DOCUMENTS

| | | | |
|---|---|---|---|
| 2001/0009907 A1* | 7/2001 | Martin et al. | 514/46 |
| 2004/0208985 A1* | 10/2004 | Rowan et al. | 427/2.25 |
| 2005/0220853 A1* | 10/2005 | Dao et al. | 424/449 |
| 2006/0121086 A1* | 6/2006 | Boyer et al. | 424/426 |
| 2006/0229713 A1* | 10/2006 | Shanley et al. | 623/1.42 |

FOREIGN PATENT DOCUMENTS

WO    WO 2008137547 A2 * 11/2008 ............. A61L 31/08

OTHER PUBLICATIONS

Ribeiro et al (Journal of Alzheimer's Disease, 2010, vol. 20, pp. S3-S15, abstract).*
Shen et al (Circulation Research, 2005, vol. 97, pp. 574-582).*
Kang et al (Molecular Pharmaceutics, published on web on May 11, 2009, vol. 6, pp. 1110-1117).*

* cited by examiner

*Primary Examiner* — Brian-Yong Kwon
*Assistant Examiner* — Mark V Stevens
(74) *Attorney, Agent, or Firm* — Barnes & Thornburg LLP

(57) ABSTRACT

Drug eluting stents (DES) useful for the treatment of restenosis are described. The stents comprise biocompatible polymers and adenosine receptor modulators.

18 Claims, 13 Drawing Sheets

DRUG-ELUTING STENTS FOR ADENOSINE RECEPTOR MODULATION

CROSS REFERENCE TO RELATED APPLICATIONS

This application claims the benefit under 35 U.S.C. §119 (e) of U.S. Provisional Application Ser. No. 61/247,731, filed Oct. 1, 2009, the disclosure of which is hereby incorporated herein by reference in its entirety.

GOVERNMENT RIGHTS

This invention was made with government support under RR013223 and HL078715 awarded by the National Institutes of Health. The U.S. Government has certain rights in the invention.

TECHNICAL FIELD

The present disclosure pertains generally to the field of medical devices. More specifically, the present disclosure pertains to drug-eluting stents for delivery of adenosine receptor modulators.

BACKGROUND AND SUMMARY OF THE INVENTION

Occlusive cardiovascular diseases, including hypertension, atherosclerosis, neointimal hyperplasia (NIHA), and restenosis, heave been reported to be closely coupled with the proliferation and migration of coronary artery smooth muscle cells (CSM). Current treatments for restenosis deal with the temporal pathological processes which involve blood coagulation, inflammation, proliferation/migration of smooth muscle cells, and endothelialization. Drug-eluting stents (DESs), composed of bare metal stents, polymer coatings and antiproliferative drugs, are used clinically to treat severe coronary atherosclerosis and have been shown to reduce in-stent restenosis. Current drugs used in DESs in the clinic generally act by non-specifically and/or non-selectively blocking all cell cycling and cell division (e.g., paclitaxel, rapamycin) in all areas near or accessible to the drugs in the stent. It has been reported that because of the lack of specificity and/or selectivity in the action of the drug on non-target cells and cell types, a delay in the recovery of a denuded endothelial layer is observed. Such delay may lead to increased thrombosis.

It has been discovered herein that stents that include adenosine receptor modulators are useful in treating vascular injury and in preventing and/or slowing the progression of restenosis. In one illustrative embodiment, devices are described herein that may be implanted in the vasculature, such as in blood vessels, and in particular coronary blood vessels. In one aspect, the devices include a stent that has a coating, where the coating includes one or more adenosine receptor modulators. In another aspect, the coating also includes a polymer or polymeric matrix. In another embodiment, the modulators are incorporated into the polymer or polymeric matrix, which is adhered to the stent. It is appreciated that the polymers and polymeric matrices described herein are desirably biocompatible.

In another embodiment at least one adenosine receptor modulator is an adenosine $A_1$ receptor antagonist. In another embodiment, at least one adenosine receptor modulator is an adenosine $A_2$ receptor agonist, such as an adenosine $A_{2B}$ receptor agonist. In another embodiment, at least one adenosine receptor modulator is an adenosine $A_2$ receptor agonist, such as an adenosine $A_{2A}$ receptor agonist. In another embodiment, at least one adenosine receptor modulator is an adenosine $A_3$ receptor modulator.

In another embodiment, the coating includes two or more adenosine receptor modulators. In another embodiment, the coating includes a combination of at least one adenosine receptor antagonist, such as an $A_1$ receptor antagonist, and at least one adenosine receptor agonist, such as an $A_2$ receptor agonist, for example an adenosine $A_{2B}$ receptor agonist and/or an adenosine $A_{2A}$ receptor agonist. It is to be understood that any and all combinations of various adenosine receptor modulators are described herein.

In another embodiment, methods for treating vascular disease or injury, such as inhibiting restenosis, are described herein, where the methods include implanting a stent described herein into a blood vessel. In one aspect, the adenosine receptor modulator is releasable from the stent in a therapeutically effective amount to treat a vascular disease or injury, such as a therapeutically effective amount to inhibit restenosis.

In another embodiment, processes for manufacturing stents are also described. The processes include applying a mixture of one or more adenosine receptor modulators and a polymer or polymer matrix to a metal stent.

DETAILED DESCRIPTION

Figure 1A:
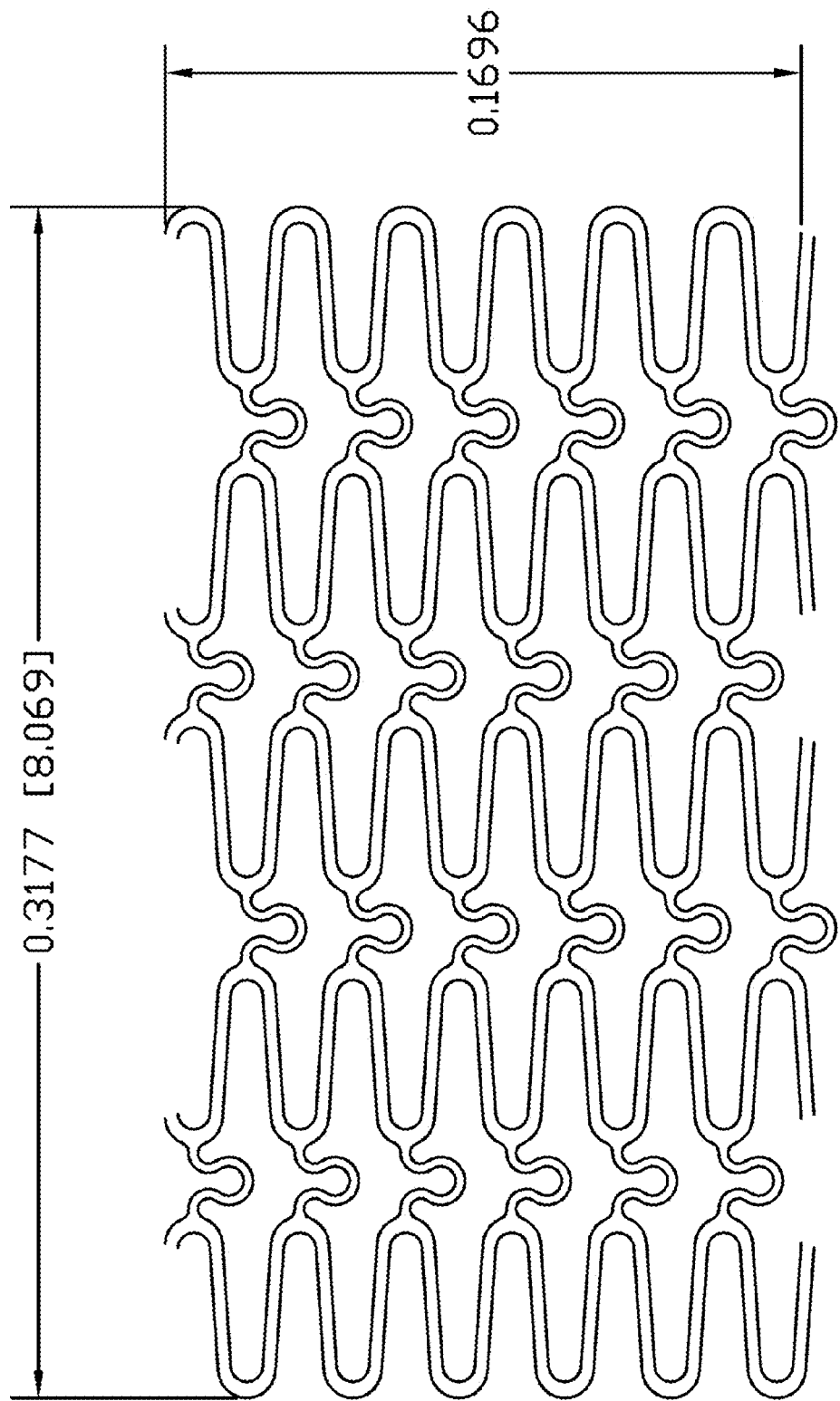
FIG. 1(A) shows the dimensions of an illustrative metal stent without a coating.
Figure 1B:
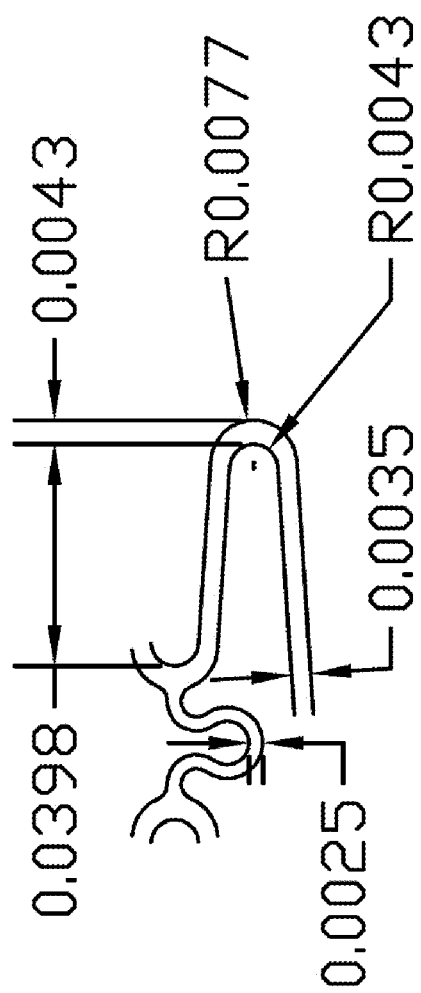
FIG. 1(B) shows the Dimensions of the repeating segment of an illustrative metal stent without a coating.

Adenosine receptors as G protein-coupled receptors are transmembrane proteins composed of seven α helical integral domain and extra/intracellular connecting loops. Four subtypes of adenosine receptors ($A_1R$, $A_{2A}R$, $A_{2B}R$ and $A_3R$) have been thus far been cloned and pharmacologically characterized. The $A_1R$ gene and protein is upregulated in macrovascular coronary artery disease (CAD) and in-stent stenosis (ISS). Proliferation of coronary smooth muscle cells (CSM) is a major contributing factor in the development of ISS.

Adenosine receptors are therapeutic targets of various diseases, such as arrhythmias, ischemia, neurodegenerative diseases, sleep disorders, diabetes, and cancer. Several selective agonists and antagonists of different adenosine receptor subtypes are known. Without being bound by theory, it is believed herein that diseases may be treated by selection of an appropriate agonist, antagonist, or both depending on differential expression of the adenosine receptor subtypes in target and non-target tissues.

It has been observed that the adenosine $A_1$ receptor is upregulated in the region of stent-induced neointima of Ossabaw miniature swine. In addition, it has been reported that the $A_1$ receptor may attenuate coronary blood flow in $A_1R$ knockout mice, though a mitogenic role has not been demonstrated. In addition, adenosine $A_{2B}$ receptor deficiency has been observed to enhance postinjury neointima formation in the vasculature in $A_{2B}$ receptor knockout mice. It has been discovered herein that the $A_{2B}$ receptor may be involved in protection against SMC proliferation in neointima formation, and mediates anti-mitogenesis in aortic vascular SMC in the rat.

Bare metal stents are deployed in coronary arteries at the site of severe, blood-flow limiting atherosclerotic lesions. However, renarrowing and blockage, i.e. in-stent restenosis, can occur mainly due to CSM proliferation.

As used herein, the term "adenosine receptor modulator" includes compounds that affect the signaling activity of one or more adenosine receptor subtypes. In one aspect, the adenosine receptor modulators bind to at least a portion of one or more adenosine receptors. It is to be understood that such adenosine receptor modulators may bind to a adenosine receptor in any manner that results in affecting the signaling activity. Such binding may be similar to, or wholly distinct from endogenous ligands. Such compounds include full agonists, partial agonists, inverse agonists, and/or antagonists of any adenosine receptor, such as the $A_1$, $A_{2A}$, $A_{2B}$, and/or $A_3$ receptors.

Illustrative examples of agonists selective for adenosine $A_{2A}$ receptors include, but are not limited to, 2-cyclohexylmethylenehydrazinoadenosine, 2-(3-cyclohexenyl)methylenehydrazinoadenosine, 2-isopropylmethylenehydrazinoadenosine, N-ethyl-1'-deoxy-1'-[6-amino-2-[(2-thiazolyl) ethynyl]-9H-purin-9-yl]-P-D-ribofuranuronamide, N-ethyl-1'-deoxy-1'-[6-amino-2-[hexynyl]-9H-purin-9-yl]-p-D-ribofuranuronamide, 2-(1-hexyn-1-yl)adenosine-5'-N-methyluronamide, 5'-chloro-5'-deoxy-2-(1-hexyn-1-yl) adenosine, N6-[2-(3,5-dimethoxyphenyl)-2-(2-methylphenyl)adenosine, 2-(2 phenyl)ethoxyadenosine, 2-[2-(4-methylphenyl)ethoxy]adenosine, 2-[2-(4-fluorophenyl)ethoxy]adenosine, 2-(2-(2-naphthyl)ethoxy)adenosine, 2-[p-(2-carboxyethyl)phenethylamino-5'-N-ethyl-carboxamidoadenosine (CGS-21680), 2-(2-cyclohexyl)ethoxyadenosine, 2-octynyladenosine (YT-146), 2-thiazolylethynyladenosine and 2-phenethylamino-5'-N-ethylcarboxamidoadenosine (CGS-21577).

Illustrative examples of agonists for adenosine $A_{2B}$ receptors include, but are not limited to, 5'-N-ethylcarboxamidoadenosina (NECA), $N^6$-cyclopentyl-adenosine (CPA), $N^6$-(2-phenylisopropyl)adenosine (R-PIA), $N^6$-4-sulfophenyladenosine (SPA), 2-chloroadenosine, 5'-N-methylcarboxamidoadenosine, 1-deoxy-1-{6-N'-(furan-2-carbonyl)-hydrazino]-9H-purin-9-yl}-N-ethyl-β-D-ribofuranuronamide, and 2-[6-amino-3,5-dicyano-4-[4-(cyclopropylmethoxy)phenyl]pyridin-2-ylsulfanyl] acetamide (BAY-60-6583).

Illustrative examples of antagonists selective for adenosine $A_1$ receptors include, but are not limited to, (±)-N6-endonorbornan-2-yl-9-methyladenine (N-0861), (±)-N6-[endo-2'-norbornyl]-8-(isopropylmethylamino)-9)-methyladenine, (±)-N6-[endo-2'-(endo-5'-hydroxy)-norbornyl]-8-(isopropylmethylamino)-9-methyladenine, 8-cyclopentyl-1,3-dipropylxanthine (DPCPX), xanthine amine congener (XAC), 8-(noradamantan-3-yl)-1,3-dipropylxanthine (NAX), 8-(cyclopentan-3-one)-1,3-dipropylxanthine (KFM19), 8-(dicyclopropylmethyl)-1,3-dipropylxanthine (KF-15372), (R)-7,8-dimethyl-2-phenyl-9-(1-phenylethyl)-7-deazaadenine, 1-propyl-3-(4-amino-3-iodophenylethyl)-8-cyclopentylxanthine (BW-A844U), (+)-(R)-[(E)-3-(2-phenylpyrazolo[1,5-a]pyridin-3-yl)acryloyl]-2-piperidine ethanol (FK453), 7-[2-[ethyl(2-hydroxyethyl)amino]ethyl]-3,7-dihydro-1,3-dimethyl-8-(phenylmethyl)-1H-purine-2,6 dione (bamiphylline), 1,3-dipropyl-8-sulfophenylxanthine (DPSPX), 1,3-dipropyl-8-[2-(5,6-exo-epoxy)-(1S,2S)-norborn-2-yl]xanthine (CVT-124), and 7,8-dihydro-8-ethyl-2-(3-noradamantyl)-4-propyl-1H-imidazo[2,1-i]purin-5 (4H)-one, and 8-(Hexahydro-2,5-methanopentalen-3a(1H)-yl)-3,7-dihydro-1,3-dipropyl-1H-purine-2,6-dione (Rolofylline).

Additional illustrative adenosine receptor modulators that may be included in the coatings described herein are described in Baraldi et al. Purinergic Signalling (2009) 5:3-19, the disclosure of which is incorporated herein by reference.

In another embodiment, at least one of the adenosine receptor modulators is a selective $A_1$ receptor antagonist. In another embodiment, one of the adenosine receptor modulators is 1,3-dipropyl-8-cyclopentyl xanthine (DPCPX). In another embodiment, at least one of the adenosine receptor modulators is a selective $A_{2B}$ receptor agonist. In another embodiment, one of the adenosine receptor modulators is 2-[6-amino-3,5-dicyano-4-[4-(cyclopropylmethoxy)phenyl] pyridin-2-ylsulfanyl]acetamide (BAY-60-6583). In another embodiment, at least two adenosine receptor modulators are included in the coating, where at least one of the adenosine receptor modulators is a selective $A_1$ receptor antagonist, and at least one of the adenosine receptor modulators is a selective $A_{2B}$ receptor agonist. In another embodiment, the coating includes DPCPX and BAY-60-6583.

As used herein, the term "therapeutically effective amount" of an adenosine receptor modulator generally refers to an amount of an adenosine receptor modulator that inhibits proliferation of coronary artery smooth muscle cells and/or facilitates growth of endothelial cells. It is to be understood herein, that the therapeutically effective amount of a mixture of two or more adenosine receptor modulators may refer both to the amount of each individual adenosine receptor modulator, and/or the total amount of adenosine receptor modulators that inhibits proliferation of coronary artery smooth muscle cells and/or facilitates growth of endothelial cells. A therapeutically effective amount may also refer to the growth of an endothelial cell layer; without being bound by theory, it is believed herein that growth of an endothelial cell layer may further secure an implanted stent in place, promote vessel healing, and/or inhibit local inflammatory responses. A therapeutically effective amount may also refer to a decrease in pERK signaling, facilitation of nitric oxide release, and/or prolonged patency of a stent. Without being bound by theory, it is believed herein that nitric oxide released from endothelial cells may inhibit the proliferation of pCSM.

As used herein, the term "inhibit" refers to preventing, blocking, stopping, and/or slowing the progression in any manner, including partially or completely reversing.

As used herein, the term "facilitate" refers to inducing, stimulating, promoting, or otherwise not inhibiting. It is to be understood that facilitating may also refer to an indirect action, where the compound or compounds intervene in a process that might otherwise lead to inhibition.

It is to be understood that all combinations of adenosine receptor modulators are described herein. It is appreciated herein that the two or more adenosine receptor modulators may have different modes of action. For example, an adenosine agonist and an adenosine antagonist may be coated on the stent. Illustratively, an adenosine $A_1$ receptor antagonist and an adenosine $A_{2B}$ receptor agonist may be coated on the stent.

Without being bound by theory, it is believed herein that the efficacy of stents described herein having a coating that includes an adenosine $A_1$ receptor antagonist is due at least in part to the ability to decrease adenosine mediated stimulation of CSM.

Without being bound by theory, it is believed herein that the efficacy of stents described herein having a coating that includes an adenosine $A_2$ receptor agonist is due at least in part to the ability of adenosine $A_2$ receptor signaling to facilitate growth of endothelial cells. In particular, adenosine $A_{2B}$ receptor signaling can result in increased release of nitric oxide and/or other anti-mitogenic substances to inhibit proliferation of CSM.

In another embodiment, the adenosine receptor modulators are mixed with a biocompatible polymer to form a coating that is applied to the stent. It is to be appreciated that biocompatible polymer may be selected from any polyurethane, poly (lactic-co-glycolic acid)-b-poly(L-lysine) (PLGA), poly(styrene-b-isobutylene-b-styrene) (SIBS) or other biocompatible polymer, including mixtures and combinations thereof. Additional illustrative biocompatible polymers are described in U.S. Patent Publication Number 2009/0043378 by Cheng et al., the disclosure of the biocompatible polymers of which is incorporated herein by reference.

A stent is a tubular structure placed inside the lumen of a duct to relieve an obstruction and/or to provide support for the vessel. Stents are typically inserted into a blood vessel in a non-expanded form and are then expanded, such as by using a balloon catheter. A major problem with stents, however, is stent-restenosis, which may be ameliorated by local delivery of adenosine receptor modulators as described herein. Without being bound by theory, it is appreciated herein that local delivery of an adenosine receptor modulator may be advantageous compared to systemic administration. Generally, with local administration, higher tissue concentrations of therapeutic agents may be achieved than with systemic administration. In addition, reduced systemic toxicity may be achieved utilizing local delivery rather than systemic administration. Also, utilizing local delivery from an implanted stent rather than repeated systemic administration of a therapeutic can overcome potential problems with patient compliance. Local stent-based therapy is therefore a means of improving the therapeutic ratio (efficacy/toxicity) of anti-restenosis, anti-inflammatory, and anti-thrombotic adenosine receptor modulators.

Illustrative stents are described herein and in U.S. Patent Publication No. 2002/0098278 by Bates et al., the disclosure of the stents of which is incorporated herein by reference.

In another embodiment, the coating may be from about 0.5 µm to about 1000 µm thick, from about 1 µm to about 100 µm thick, or from about 5 µm to about 50 µm thick.

Figure 2A:
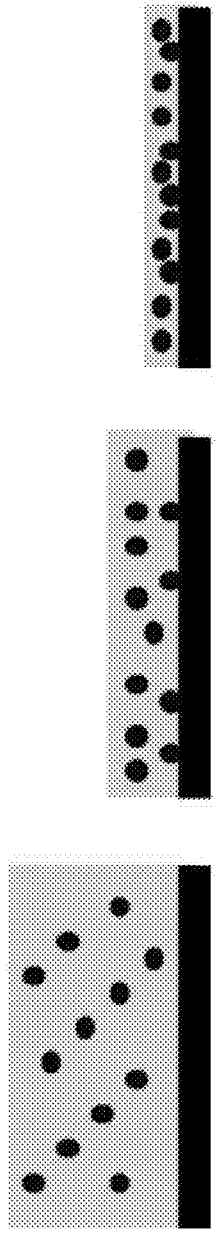
FIG. 2 shows a schematic presentation of the coating condition and expected film thickness. (A) Constant drug surface density using different drug concentrations in the coating solution. (B) Constant drug concentration in the coating solution with different drug surface densities. The first number presents the drug composition of a sprayed solution, and the second number is the targeted drug surface density.
Figure 2B:
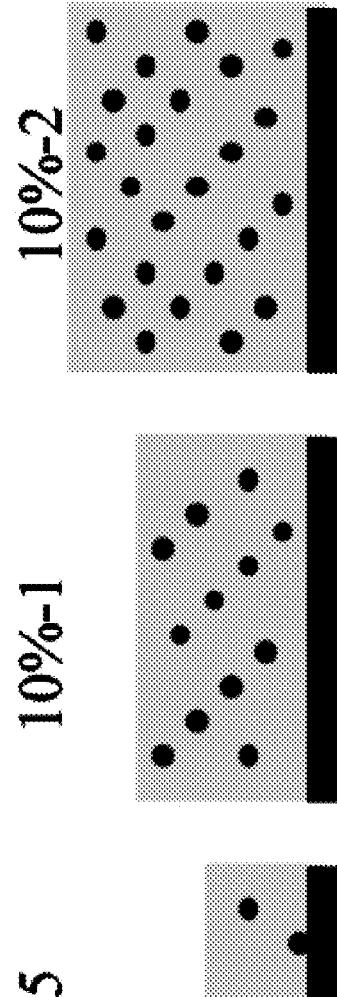

In another embodiment, the surface density of the adenosine receptor modulators on the coating may be from about 0.01 to about 20 µg/mm$^2$, from about 0.1 to about 5 µg/mm$^2$, or from about 0.5 µg to about 2 µg/mm$^2$. Surface density refers to the weight of an adenosine receptor modulator distributed over the surface of the coating, as shown in FIG. 2.

It is to be understood that the coating is not necessarily uniform, and may vary from the interior to the exterior, and/or in various regions of either or both the interior and exterior. Uniformity, or the lack thereof, may be evaluated by measuring the thickness, loading, surface density, or other physical parameter of the coating.

Without being bound by theory, it is appreciated herein that the length of time over which the compounds forming part of the stent are released may be desirably shorter or longer depending upon the nature of the injury or disease being treated. In one aspect, the adenosine receptor modulator is released from the stent over a period of from about 2 days to about 500 days, or from about 7 days to about 100 days, or from about 20 days to about 50 days.

It is also appreciated herein that the release characteristics of the stents described herein may be tested, optimized, and or standardized in an in vitro setting. In another illustrative embodiment, an adenosine receptor modulator is releasable from the polymer over a period of several days when tested in vitro in a solution of phosphate buffered saline (PBS). In one illustrative embodiment, an adenosine receptor modulator is released for at least about 7 to about 120 days when the mixture is released into PBS. Preferably, an adenosine receptor modulator is released for at least about 14-60 days into PBS. More preferably, the adenosine receptor modulators are released for at least about 28 days. Preferably, an adenosine receptor modulator is released from the coating at a per day average rate of from about 0.1% to about 5% of initial adenosine receptor modulator weight. More preferably, an adenosine receptor modulator is released at an average rate of from 0.5% to about 1.5% of initial adenosine receptor modulator weight per day.

According to another embodiment, processes for manufacturing a drug-eluting stent are disclosed. The processes comprise applying a mixture of one or more adenosine receptor modulators and a biocompatible polymer to the surface of the stent. Illustratively, the mixture may be applied by any conventional method, including electrostatic spraying, dipping, and the like.

It is to be understood herein that growth of endothelial cells over the stent area may be beneficial for long-term patency of the DES. Thus, it is desirable to develop a treatment for restenosis that has specific antiproliferative effects on CSM and/or facilitative effects on growth of endothelial cells. It is discovered herein that local application of adenosine receptor modulators can inhibit proliferation of CSM and facilitate growth of endothelial cells.

There are numerous mechanisms involved in restenosis, including platelet aggregation, which has been shown to be increased in diabetic dyslipidemic swine. Platelets release growth promoting and vasoactive molecules such as ATP, which rapidly breaks down to adenosine and stimulates coronary smooth muscle and endothelium via several adenosine receptor-coupled signaling pathways. Key steps in restenosis involve de-differentiation of the CSM from their normal contractile phenotype (cCSM) to a proliferating, phenotypically modulated cell (pCSM). Without being bound by theory, it is believed herein that when stimulated by adenosine, A1 receptors mediate increases in DNA synthesis and proliferation of pCSM in part via a p-ERK pathway. A healthy endothelium is anti-thrombogenic and may attenuate smooth muscle proliferation by release of nitric oxide (NO) and other anti-mitogens. Localized delivery of adenosine receptor modulators are useful to specifically target adenosine receptor mediated mechanisms involved in restenosis in the endothelium and smooth muscle, as described herein.

The role of adenosine $A_1$ receptors in CSM proliferation has been studied in the Ossabaw miniature swine model which has metabolic syndrome and type 2 diabetes. The Ossabaw miniature swine model is advantageous in that simple diet induces atherosclerosis and hyperplasia in a local stent region, mimicking those in human patients. This animal model allows for the study of treatment of restenosis by use of adenosine receptor modulators. Previous studies indicate that porcine CSM express $A_1$ $A_{2A}$, $A_3$ receptors; whereas mRNA levels for $A_{2B}$ receptors are barely detectable. Adenosine receptors are also differentially expressed on human endothelial cells. Human CSM express $A_1$, $A_{2A}$, and $A_3$ receptors. In human endothelial cells, adenosine $A_{2A}$ and $A_{2B}$ receptors have been found to be mainly expressed, $A_3$ receptors have not, and $A_1$ receptor expression is controversial. When $A_1$ receptor expression has been found in human artery endothelial cells the functional effect of $A_1$ receptor stimulation has been to decrease nitric oxide production. The adenosine $A_1$ receptor mediates mitogenic effects of adenosine in CSM in vitro via activation of the ERK1/2, JNK, PI3K-AKT signaling pathways. An in vivo study shows that the adenosine $A_1$ receptor is up-regulated in stent-induced neointimal hyperplasia in coronary artery of Ossabaw miniature swine. Because adenosine receptor subtypes are expressed in cardiovascular regions, selective agonists and antagonists of adenosine receptors can be employed to target diseases at specific local regions.

While the invention is susceptible to various modifications and alternative forms, specific embodiments will herein be described in detail. It should be understood, however, that there is no intent to limit the invention to the particular forms described, but on the contrary, the intention is to cover all modifications, equivalents, and alternatives falling within the spirit and scope of the invention.

EXAMPLES

EXAMPLE. The physiochemical properties of an illustrative adenosine receptor modulator, DPCPX, were examined for loading into a polymer layer of a stent and the drug release profiles were studied to understand the release mechanisms. DPCPX eluted from polyurethane (PU) film was used to examine whether it was able to inhibit proliferation of subcultured CSM from Ossabaw swine through blockage of adenosine $A_1$ receptor mediated signaling. It was found that 1,3-dipropyl-8-cyclopentyl xanthine (DPCPX), which is a modified xanthine, is effectively eluted from polymers used in drug eluting stents (DES) and is able to inhibit CSM proliferation. It was also found that DPCPX eluted from polyurethane film was able to inhibit proliferation of subcultured CSM from Ossabaw swine through blockage of adenosine $A_1$ receptor mediated signaling EXAMPLE. 2-Chloro-N-6-cyclopentyladenosine (CCPA) and 1,3-dipropyl-8-cyclopentyl xanthine (DPCPX) were purchased from Tocris (Ellisville, Mo.). Segmented polyurethane (PU, Cardiomat 610) was purchased from Polymer Technology Group, Inc. (Berkeley, Calif.). Collagen type I was purchased from Inamed (Purecol, Fremont, Calif.). Bare metal stents (BMSs) were designed by the authors, and were manufactured by Burpee materials technology (Eatontown, N.J.). Starting material was 316 L stainless steel tubing, either 1) 0.052 inch outer diameter and 0.0043 inch wall thickness, which yielded a final wall thickness of 0.0033 to 0.0035 inches or 2) 0.054 inch outer diameter and 0.0053 inch wall thickness, which yielded a final wall thickness of 0.0043 inches.

EXAMPLE. A series of DPCPX/PU solutions were prepared in tetrahydrofuran (THF) (total solid concentration: 0.5 w/v %). The ratio of DPCPX/PU was adjusted to 10, 20, and 30 wt %. The solution of DPCPX and PU was coated on BMSs using an electrostatic spray method. The BMS had a surface area of 51.69 $mm^2$, 8 mm in length and 4 mm of diameter upon expansion. A stent was mounted on a mandrel connected with a rotator and a transverse system. The electrostatic spray conditions were fixed: 0.02 mL/min of flow rate, 8.0-10.0 kV of high voltage, and 10 psi of air flow. The distance between the stent surface and the spray nozzle was set as 1.5 cm. The amount of drug/polymer coated on a stent was confirmed by weight measurement after drying residual solvent.

The adenosine receptor modulator, DPCPX (1 mg), was added to 1 mL of distilled water at various pH ranging from 3 to 11. The pH of distilled water was adjusted with 0.01 N of HCl or 0.1 N of NaOH. Samples were vigorously stirred for 48 h at 120 rpm at 37° C., and then filtered with a nylon syringe filter (pore size: 0.2 μm). The DPCPX release from the dilated DESs was performed in phosphate buffered saline (PBS) at 120 rpm at 37° C. Medium (1 mL) from the sample was taken at predetermined time periods, and the remaining medium was aspirated to be replaced with 2 mL of fresh medium. Samples were analyzed for DPCPX solubility and released DPCPX using high performance liquid chromatography (HPLC) (AGILENT 1100 series) with UV detection at 227 nm. Samples were run with 1 mL/min of flow rate at 25° C., with methanol and water (6:4 ratio) used as the mobile phase.

DPCPX and PU solutions (10 wt %) were prepared in THF. The ratio of a drug to a polymer was varied from 0 wt % to 30 wt % of the total solid. The solution was dropped on a 15 mm round cover glass and was spin-coated at 1000 rpm. The coated films on the cover glass were dried under vacuum for 24 h to remove residual solvent. A drug eluting film coated on the cover glass was placed in each well of a 24-well plate for a cell culture study.

EXAMPLE. Hearts were harvested from Ossabaw pigs. Coronary arteries dissected from the hearts were placed in a physiological buffer. Porcine CSM were enzymatically dispersed from coronary arteries using collagenase solutions. Primary cultured CSM were subcultured at 37° C. with 5% CO2 in DMEM containing 10% fetal bovine serum (FBS). CSM cultured with 80% confluence were used between passage 4 and 10.

The CSM were seeded on the surface of type I collagen that was gelated on the DPCPX-loaded PU film. The DPCPX-loaded PU films with various drug/polymer ratios and pure PU film as a control were placed in 24-well plates. Collagen solution was prepared by mixing eight parts of PURECOL (3 mg/mL) with one part of 10×PBS. The pH of the collagen solution was adjusted to 7.4 by adding 0.01 N HCl and 0.1 M NaOH. Collagen solution (300 μL) was added to each well containing the PU/DPCPX-coated cover glass. After 30 min of incubation at 37° C., collagen matrix/DPCPX-loaded PU film was washed with PBS and filled with DMEM containing 10% FBS. Subcultured CSM were suspended by trypsinization, counted and seeded on the collagen matrix/DPCPX-loaded PU film in 24 wells. Seeding density was 4,000 cells per well in DMEM containing 10% FBS in a 24-well plate. CSM were stimulated in the presence of CCPA for 2 days.

After 4 days, cell proliferation was estimated using an MTT cell growth assay kit (Chemicon International). The tetrazolium compound 3-(4,5-dimethylthiazol-2-yl)-2,5-diphenyltetrazolium bromide (MTT, 20 μL) was added to 100 μL of fresh DMEM. The CSM were incubated in the solution for 4 h at 37° C. The absorbance was read at 490 nm, which was directly proportional to the number of living cells. The measured absorbance in each treatment group was compared to the percent of control.

EXAMPLE. The morphology and coating integrity of a DPCPX and PU coated stent were characterized using scanning electron microscopy (JEOL JSM-840; Jeol USA). Stents were mounted to aluminum stubs and coated with gold palladium in argon gas using a sputter coater (HUMMER I; Anatech Ltd.). Coated stents were observed and imaged using SEM with an accelerating voltage of 4 kV, a probe current of $3 \times 10^{-11}$ A, and a working distance of 15 mm.

EXAMPLE. Cells were fixed with 4% formalin and stained with propidium iodide solution. Stained CSM were observed with fluorescence confocal laser scanning microscopy (CLSM) (model MRC-1024, BIO-RAD) equipped with a krypton/argon laser and a Nikon DIAPHOT 300 inverted microscope.

EXAMPLE. For the release study, the solubility of the adenosine receptor modulator DPCPX was measured in water, PBS (pH 7.0), and PBS/0.05 wt % Tween 20 (pH 7.0). DPCPX (1 mg) was added to 1 mL of each medium and stirred for 48 h at 37° C. The solubility of DPCPX measured in water, PBS, and PBS/0.05% Tween 20 at pH 7.4 was 1.62±0.12, 1.69±0.72, and 1.63±0.08 μg/mL, respectively. There were no statistical differences among the solubilities. The solubility of DPCPX was also measured as a function of pH in water, ranging from 3 to 11. The DPCPX solubility (approximately 1.6 μg/mL) in water was not significantly changed between pH 3 and 9, while it reached 38.1±2.3 μg/mL at pH 11. The solubility of DPCPX in water at pH 11 was 28 times higher than the solubility at pH 3-9. If such a high solubility increase occurred at pH closer to the physiological pH, the aqueous solution at that pH could have been used as a release medium providing a sink condition. Because pH 11 was too far away from the physiological pH, subsequent in vitro release experiments of DPCPX-eluting stents were carried out in PBS at pH 7.4.

EXAMPLE. Bare metal stents were coated with DPCPX/PU using an electrospray coating method. The solid concentration of the polymer and the drug in spraying solution was 0.5 wt % in THF, and the ratio of drug to polymer was varied from 10 to 30 wt %. The density of DPCPX per stent (μg/mm$^2$) was varied by changing the drug/PU ratio in the spraying solution and the spraying time. The amount of coated polymer/drug was calculated by measuring the weight of stents before and after coating to obtain the desired drug density per stent. Images of DPCPX-eluting stents were taken with brightfield microscopy, SEM, and CLSM. DPCPX eluting stents coated with PU had no web formation along the wire and the smooth surface texture of the PU film was observed.

After expansion of a DPCPX-coated stent, no delamination or peeling-off of the PU film was observed, indicating that a DPCPX/PU coated stent can withstand the compressibility and the strain associated with expansion of the stent. The SEM image indicated that the film surface was smooth and no drug crystals were formed, indicating that DPCPX was well integrated in the PU matrix without separation. The thickness of the PU film coated on a BMS was measured by staining the film with 0.01 wt/v % of nile red in water. The orthogonal images of a stent strut were taken with CLSM. The variance of film thicknesses is presented in Table 1, as DPCPX-eluting stents were coated under different conditions.

TABLE 1

Thickness of films prepared using different coating conditions.

|  | drug concn % (w/w) | av thickness (μm) | drug density (μg/mm$^2$) |
|---|---|---|---|
| 10%-0.5 | 10 | 19.2 ± 0.8 | 0.5 |
| 10%-1 | 10 | 23.5 ± 0.9 | 1 |
| 10%-2 | 10 | 37.6 ± 1.4 | 2 |
| 20%-1 | 20 | 14.9 ± 1.7 | 1 |
| 30%-1 | 30 | 6.9 ± 0.5 | 1 |

A schematic representation of the targeting dose density and the resulting film thickness is presented in FIG. 2. The first and the second numbers in the notations in Table 1 and FIG. 2 represent the drug/PU ratio in the spraying solution and the drug surface density, respectively.

For example, 10%-1 indicates the DPCPX concentration of 10 wt % and the drug surface density of 1 μg/mm$^2$. A series of stents (set A) were prepared with varied drug/PU ratios (10, 20, and 30 wt %) at the constant drug surface density of 1 μg/mm$^2$. The polymer thicknesses of 10%-1, 20%-1, and 30%-1 stents were 23.5±0.9, 14.9±1.7, and 6.9±0.5 μm, respectively. The film thickness was decreased with the increase in the drug/PU ratio of the spraying solution, because the total drug density was maintained constant for each stent. Another series of stents (set B) were coated with the spraying solution with 10 wt % DPCPX/PU ratio and the drug surface density was varied as 0.5, 1, and 2 μg/mm$^2$ by adjusting the duration of spray coating. The measured thicknesses of 10%-0.5, 10%-1 and 10%-2 were 19.2±0.8, 23.5±0.9, and 37.9±1.4 μm, respectively. The film thickness was increased with the increase of the drug density at the constant DPCPX/PU ratio in the spraying solution.

Figure 3B:
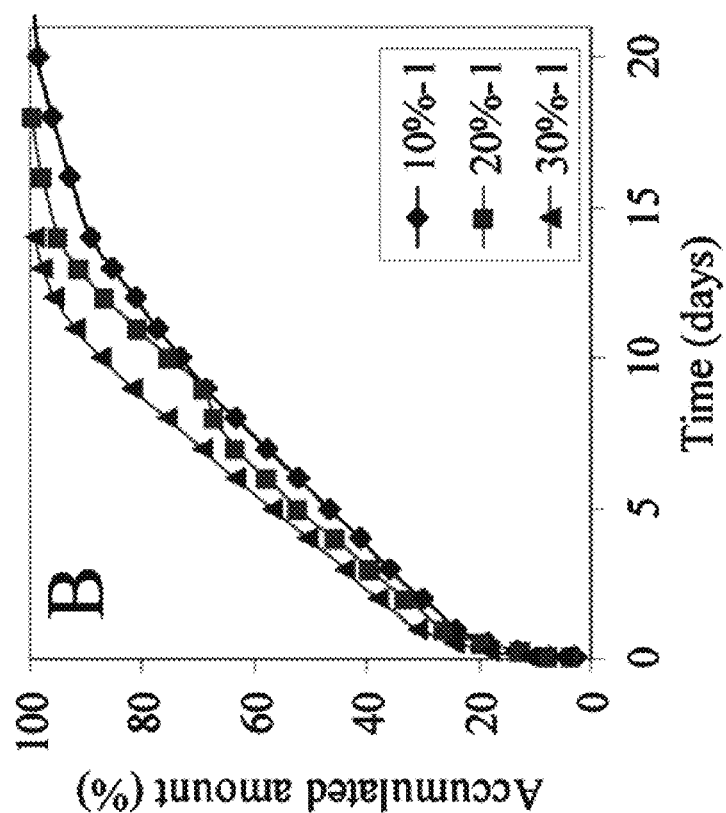
FIG. 3 shows DPCPX release profiles in the cumulated total amount (A and C) and in the percent release (B and D) from different formulations. The stents were coated with solutions of different concentrations for the same drug surface density (A and B). The stent coated with varied drug surface density using the same 10% DPCPX spraying solution (C and D).
Figure 3A:
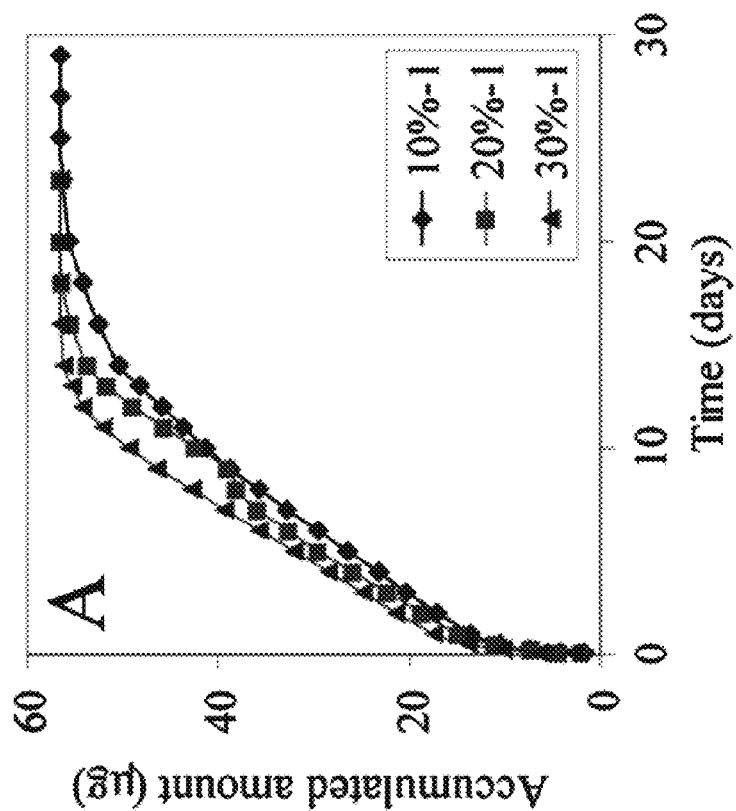
Figures 3C, 3D:
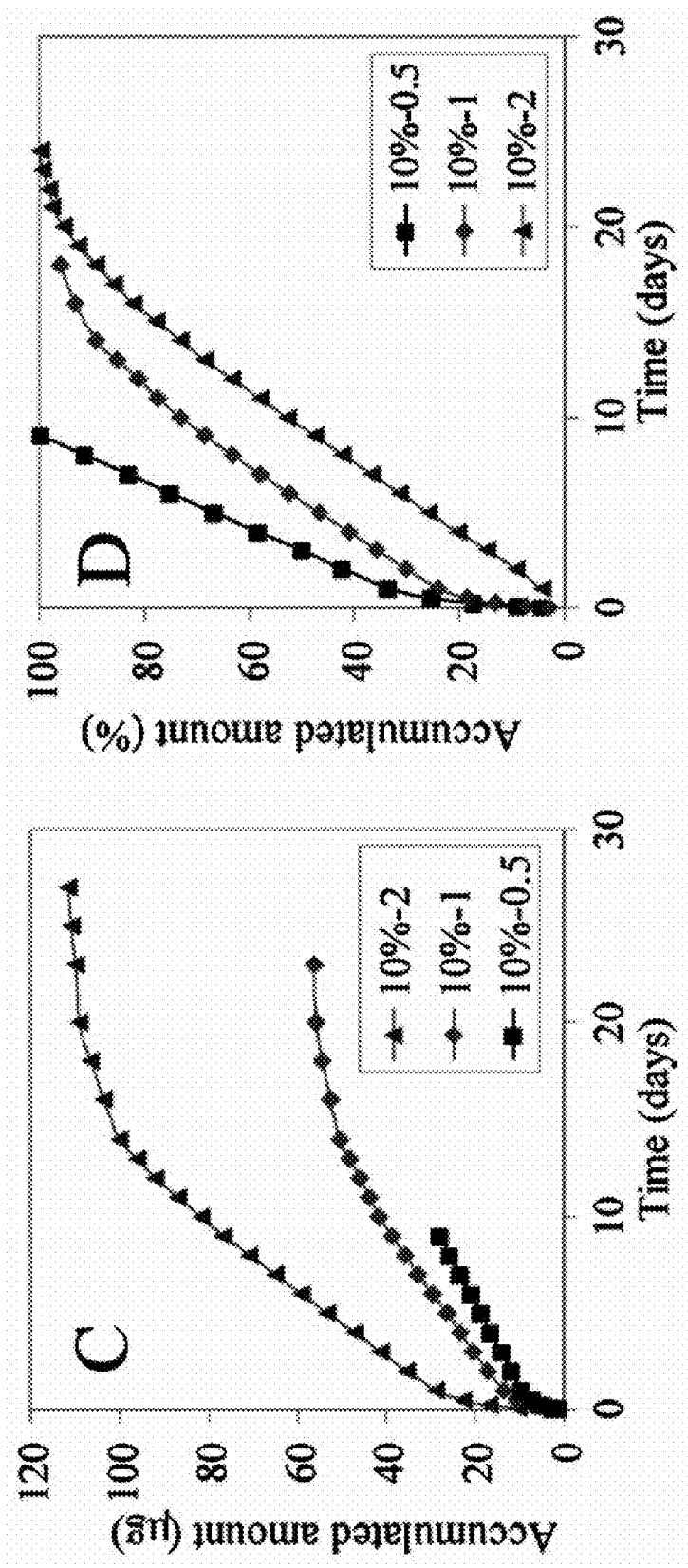

The drug elution profiles of the two different sets of PU films were examined instead of expanded state of stents. As shown in FIG. 3, for all PU-coated stents, DPCPX release was nearly linear after the initial burst release on the first day. The release rate was slightly accelerated with the increase in the drug/PU ratio on the stent coated at the constant drug density of 1 μg/mm$^2$ (30%>20%>10% DPCPX/PU ratio). The ratio between the drug and PU in the spraying solution, however, did not change the extent of release rate significantly (FIG. 3-A,B) as compared with paclitaxel release from the poly (styrene-b-isobutylene-b-styrene) (SIBS) matrix for the same formulation condition in a previous study.

The periods of DPCPX release were almost the same for the formulations in the range of 14 days. For the second set of release studies, the duration of DPCPX release was prolonged, as the total drug amount loaded on the stent and the drug density were increased at a constant drug/PU ratio (10 wt %). The durations of release were 9 days for 10%-0.5, 23 days for 10%-1, and 28 days for 10%-2, respectively (FIG. 3-C,D).

The drug release rate was also accelerated with the increase of the drug surface density at the constant drug/PU ratio (10 wt %) of the spraying solution.

As the total drug amount or the drug surface density was increased, the film on the stent became thicker. The increased film thickness resulted in drug diffusion for longer distance and thus for a longer period of time. Since only the duration of spraying time was adjusted, using the spraying solution with the constant drug/PU ratio (10 wt %), the drug concentration (i.e., volume density) is similar in all three cases (10%-0.5, 10%-1, and 10%-2), and drug distribution is uniform throughout the film thickness. Thus, the film thickness and the total drug amount per stent were the major components to modulate the drug release from the DPCPX/PU-coated stents, because release was dominated by diffusion through the polymer film.

The signal pathways relevant to adenosine-induced CSM mitogenesis have been studied using various pharmacological agents. Stimulation of CSM by adenosine and other agonists increases the phosphorylation levels of extracellular signal regulated kinase 1/2 (ERK1/2), jun N-terminal kinase 1/2 (JNK1/2) and PI3K-AKT in a dose-dependent manner, indicating that adenosine activates the ERK, JNK and PI3K-AKT signaling pathways. CCPA, an $A_1R$ selective agonist, is useful to study adenosine activation of mitogenic signaling pathways.

Both adenosine and CCPA increase DNA synthesis, protein synthesis, and cell number in porcine CSM. In contrast, DPCPX, an $A_1R$ selective antagonist, significantly decreases adenosine-induced ERK, JNK, and AKT phosphorylation in a dose-dependent manner.

EXAMPLE. The effects of the adenosine receptor modulator, DPCPX, released from PU films on the CSM proliferation in vitro were evaluated to find desirable conditions for developing a DPCPX-eluting stent. For the cell culture study, DPCPX-loaded PU films were casted on cover glass by spin coating. The drug amount in the PU film on each cover glass was 9.8±1.36 μg for 10%, 25.8±0.78 μg for 20%, and 52.1±0.94 μg for 30% DPCPX, respectively. CSM did not grow on the PU film, and thus, a porous collagen gel matrix was placed on the DPCPX-loaded PU film. The collagen matrix was about 300 μm in thickness as measured from autofluorescence of an orthogonal image of collagen matrix taken with confocal laser scanning microscopy. Then, SMCs were seeded on the collagen gel matrix. The collagen matrix was highly porous, and did not impede the drug diffusion to medium. CSM attached to the collagen gel matrix and proliferated. SMCs are embedded in the extracellular matrix in the coronary artery, and a drug from a stent would need to diffuse through the extracellular matrix to affect SMC proliferation. Thus, the experimental design using DPCPX loaded PU films coated with collagen gel matrix mimics the physiological condition for testing the effect of DPCPX elution on CSM.

Figure 4:
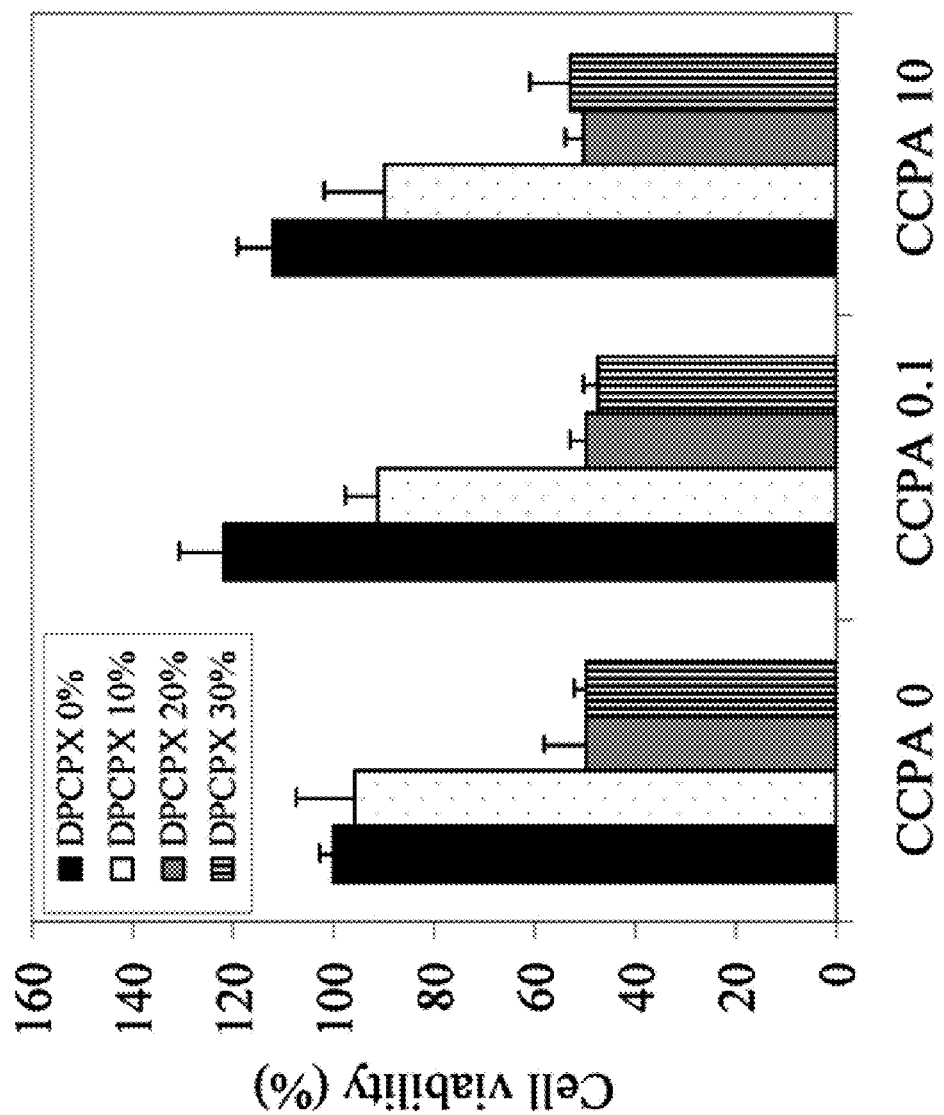
FIG. 4 shows SMC viability analyzed by MTT assay in the presence of different CCPA concentrations.

EXAMPLE. CSM antiproliferation effects of an adenosine receptor modulator, DPCPX, in the absence or presence of CCPA were examined by monitoring cellular DNA synthesis via [$^3$H]-thymidine uptake, protein synthesis via [$^3$H]-leucine uptake, and consequent live cell number via MTT assays as in previous studies (Shen, J. Z. et al., Circ. Res. (2005), 96(9), 982-990 & Shen, J. Z. et al., Circ. Res. (2005) 97(6), 574-582. Since the antiproliferative effect of DPCPX at the molecular level was already shown in CSM culture in vitro, only the live cell number via MTT assay was examined. CSM were exposed to CCPA at different concentrations (0, 0.1, 10 μM) for the first 2 days. After 2 days, CCPA was removed by replacing the medium with fresh medium without CCPA. At the same time, DPCPX, an $A_1R$ selective, antagonist was competitively exposed to CSM by diffusion from the PU film through a collagen gel layer. The first control, with no CCPA exposure in medium and no DPCPX diffusion from the PU film, reached 80% confluence of CSM at day 4. Therefore, the effects of DPCPX on CSM proliferation were evaluated by CSM proliferation at day 4 using the MTT assay, as shown in FIG. 4. The second control, with CCPA exposure and no DPCPX release, showed increased CSM viability (121.8% at 0.1 μM CCPA and 112.2% at 10 μM CCPA), as compared with the first control (100%, no CCPA, no DPCPX).

The increased cell viability in the presence of CCPA indicates that cell proliferation was augmented by increased DNA and protein synthesis that were stimulated by CCPA via the activation of $A_1R$ receptors. At 10% DPCPX loading, viability was 95.9% at 0 μM CCPA, 91.23% at 0.1 μM CCPA, and 89.6% at 10 μM CCPA. These values are not much different from the cell viability of the first control (100%, no DPCPX, no CCPA). CSM viability was not changed significantly, regardless of the CCPA concentration, compared with the first control (no CCPA, no DPCPX).

The total drug amount of 10% DPCPX-loaded film on the glass was 9.8 μg in each well, which is 5.9 times lower than that total amount DPCPX of the 10% loaded stent. The majority of DPCPX might have been depleted during an initial burst in the first few days. Thus, after refreshing the medium without CCPA, the drug amount released from 10% DPCPX loaded PU film might not have been sufficient to affect cell proliferation of CSM. In contrast, the competitive exposure of DPCPX in the presence of 0.1 μM CCPA in the medium resulted in reduced CSM proliferation, showing that viability was 25% lower than that by only CCPA stimulation (0.1 μM CCPA, no DPCPX). This result indicates that DPCPX performed as an effective antagonist of $A_1R$ receptor in this experiment, competitively acting at adenosine receptors against CCPA. DPCPX release from the 20% and 30% DPCPX-loaded films without exposure of CCPA showed that cell viability was significantly decreased to 49.8%, compared with the control (no CCPA, 10% DPCPX). In addition, exposure of 0.1 μM and 10 μM of CCPA did not alter the effect of DPCPX, showing reduced cell viability of approximately 50%. This result is consistent with reports of CCPA-induced DNA and protein synthesis inhibition by DPCPX in a concentration-dependent manner.

DPCPX released from the PU film was effective in reducing CSM proliferation and viability. Competitive exposure with the $A_1R$ agonist, CCPA, confirms the selective effect of DPCPX antagonism of the $A_1R$. Cell morphology and confluence were observed by staining CSM with propidium iodide and CLSM. The spindle shape of SMC was maintained in the presence of CCPA/DPCPX compounds. The confluence was affected by addition of an agonist or an antagonist. The SMC growth was enhanced in the presence of CCPA without DPCPX, whereas confluence of SMC was reduced in presence of CCPA/DPCPX. The presence of DPCPX diminished SMC proliferation in vitro even in the presence of CCPA. The images showed similar confluence as found in the MTT assays of cell viability.

The DPCPX/PU films for in vitro cellular experiments were coated by spin-coating. Even though the composition of drug/polymer is the same as that of the stent-coated films, the coated films of 1-3 μm in thickness are thinner, since the excess of drug/polymer solution was removed during the coating process due to centrifugal force. In contrast, stents coated by electrospray were coated with fine mists for 5-10 min. Thus, drug distribution through the depth of the film might not be identical. Nevertheless, the in vitro cellular study demonstrated that varying DPCPX release amounts affected cellular growth rate.

The experiments described herein demonstrate that $A_1R$ mediates mitogenesis in CSM. The net proliferative or antiproliferative effects adenosine receptor subtype activity in a local region of SMC depends on the balance between the expression level and signaling efficiency of the receptors. There is evidence of elevated $A_1R$ expression in local stent regions. To combat restenosis, drugs specific to the local cellular signal pathway for reducing SMC proliferation and/or facilitating endothelial cell growth in the stent region can be employed.

Adenosine receptor modulators released from a stent, for example, the adenosine $A_1$ receptor antagonist DPCPX, may be used to prevent proliferation of CSM. Illustratively, released DPCPX successfully prevented SMC proliferation even in the presence of CCPA, an agonist of $A_1$ receptor.

In the experiments described herein, DPCPX, which acts on the $A_1$ receptor that is differentially expressed on porcine coronary artery endothelial cells and SMCs, was used as an exemplary adenosine receptor modulator in DESs. DPCPX was successfully formulated within a PU polymer matrix without disintegration of drug from the polymer matrix. Smooth integration of the drug was observed from SEM pictures. Release profiles from DPCPX-eluting stents showed sustained release of DPCPX.

In the drug release study, 2 mL of PBS buffer was used as a release medium which was replaced with a fresh solution every day. Release profiles may be partially affected by dissolution-limited release in addition to diffusion-limited release. Previous studies used 1.5 mL of medium with addition of 10% ethanol or 1.5 mL of PBS with 0.005% Tween 20 per stent. Addition of ethanol in the release medium removed the solubility limitation, but ethanol affected the release profiles as confirmed in the accelerated release studies; thus, ethanol was not used in this study.

EXAMPLE. The Ossabaw miniature swine model is a useful animal model for studying the efficacy of drugs that are released from drug eluting stents. Stenting in the coronary artery increases expression of the $A_1$ receptor, as compared with the non-stented coronary artery.

Figure 5A:
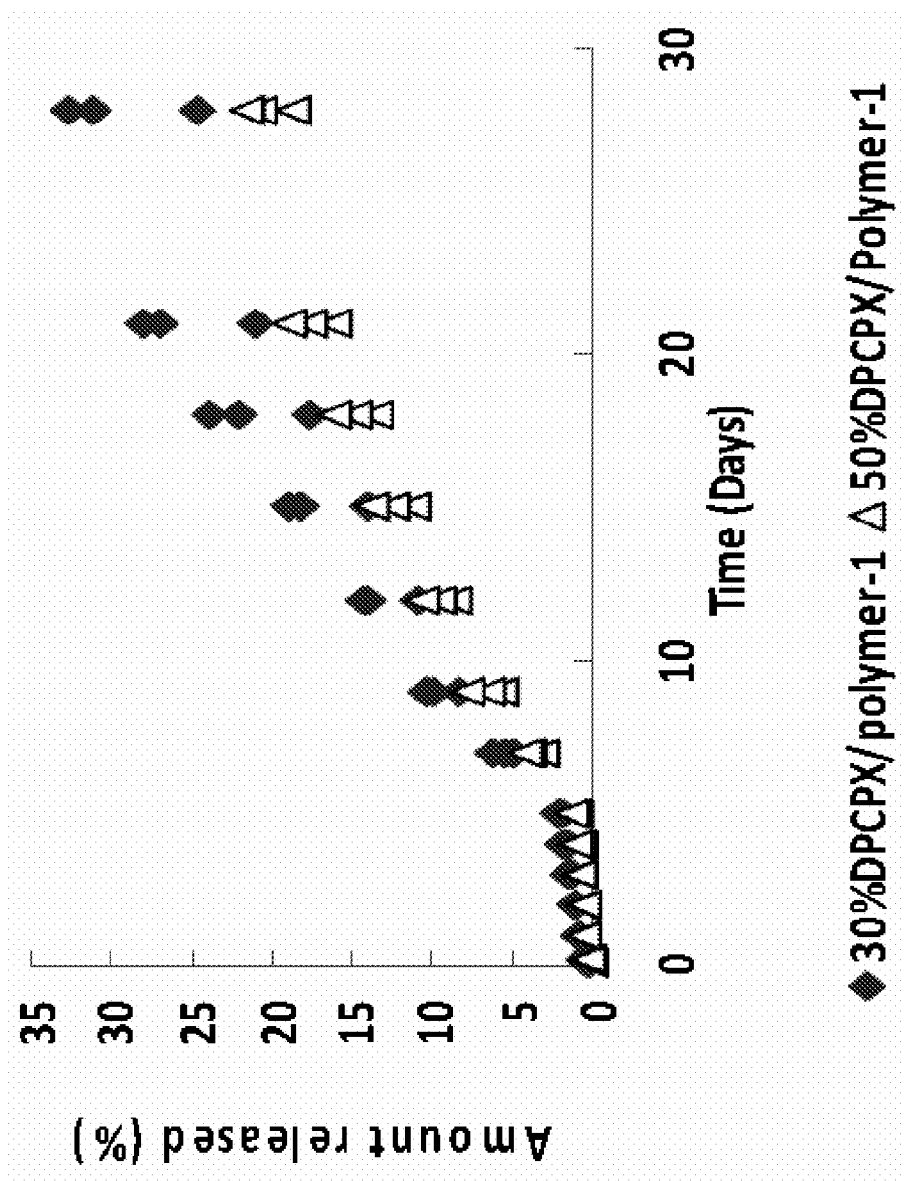
FIG. 5 shows in vitro elution kinetics of DPCPX-eluting stents (A) DPCPX with polymer-1 and (B) DPCPX with polymer-2.
Figure 5B:
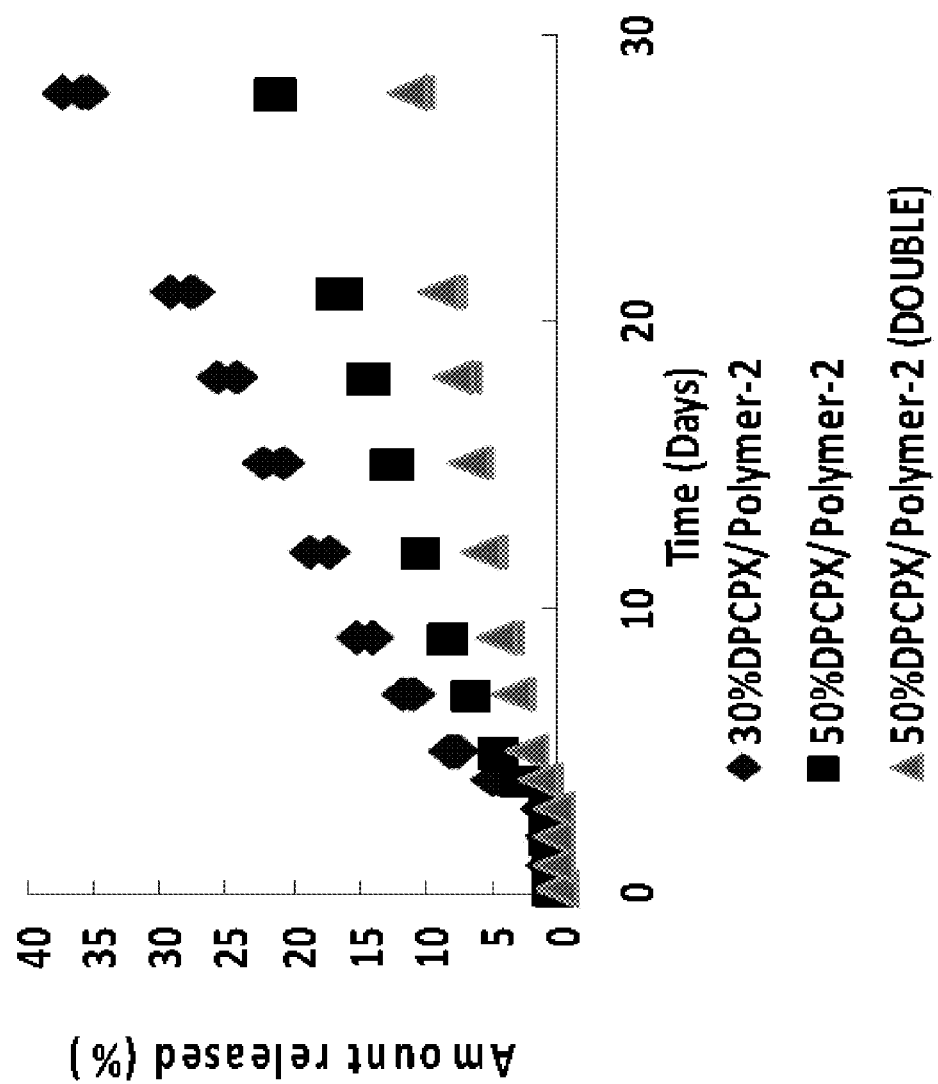

Stainless steel stents were coated with polymer and DPCPX in concentrations that optimized in vitro elution kinetics of DPCPX (FIG. 5). Stents used for in vivo testing were coated with 300 μg DPCPX and 700 μg PLGA (poly (lactic-co-glycolic acid)-b-poly(L-lysine)) polymer. $A_1R$ selective antagonist-DPCPX was dissolved in THF along with polymer-1 and polymer-2. The solutions were spray coated on stainless steel stents. The coated stents were stored in PBS buffer and sampled at different time intervals. The amounts of released DPCPX were analyzed using HPLC. Two DPCPX/Polymer ratios, 30% and 50%, were used to determine a desirable release profile. A second coating was also performed for DPCPX in polymer-2 (PLGA) at a ratio of 50%. The release of DPCPX was sustained over the entire 28 day period that was examined, and did not appear to be diminishing.

Under angiographic guidance, polymer- and DPCPX-eluting stents were placed in either left circumflex (CFX) or left anterior descending (LAD) artery of anesthetized male Ossabaws by random assignment.

A stainless steel stent deployment was utilized to cause vascular injury, which leads to coronary neointima formation (in-stent stenosis) in lean Ossabaw swine and in Ossabaw swine with metabolic syndrome (also known as pre-diabetes). Stents were inflated to 1.1× of lumen diameter. The right coronary artery (RC) served as a non-stented control. Pigs were allowed to recover for 4 weeks, then sacrificed, and coronary arteries were harvested for tissue analysis.

Figures 6A, 6B:
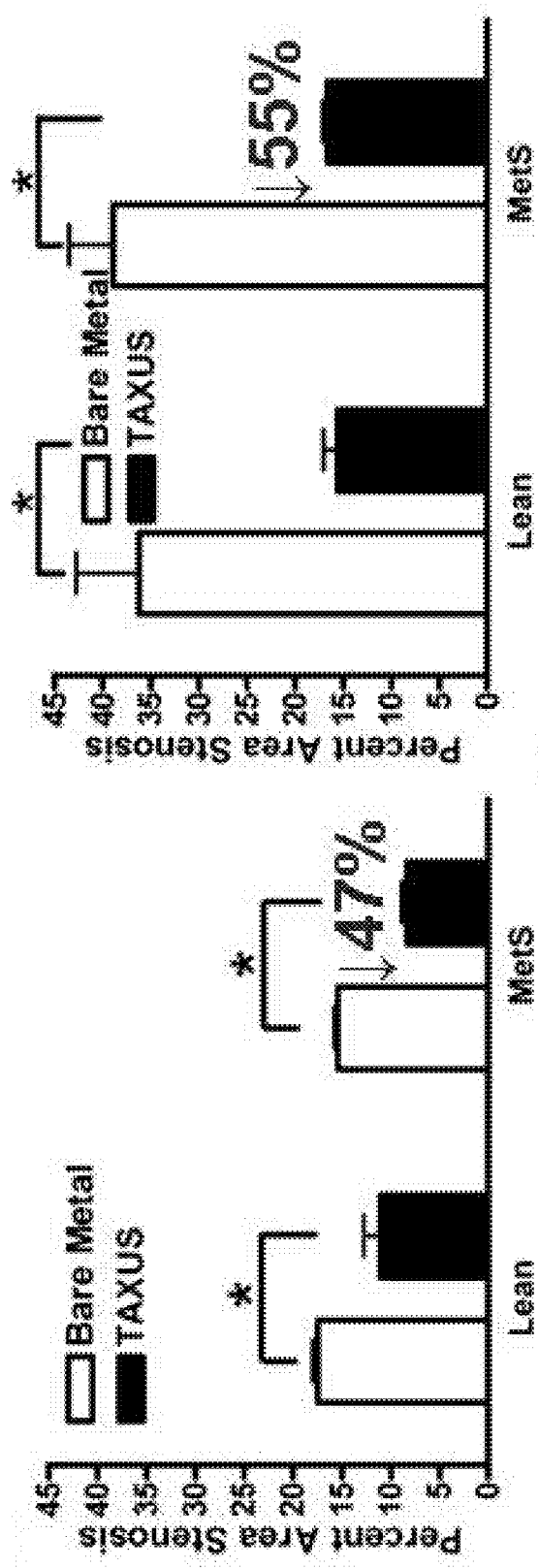
FIG. 6 shows in-stent stenosis in pigs treated with bare metal and paclitaxel stents or polymer-coated and adenosine receptor modulator (DPCPX, $A_1$ receptor antagonist) eluting stents; * indicates statistical significance (p<0.01) of the drug eluting stent compared to the bare metal stent or polymer only stent.
Figure 6C:
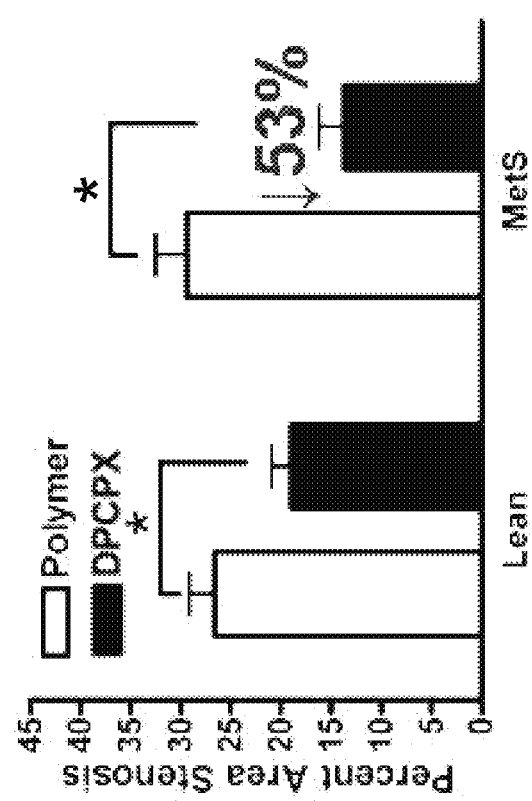
Figure 6D:
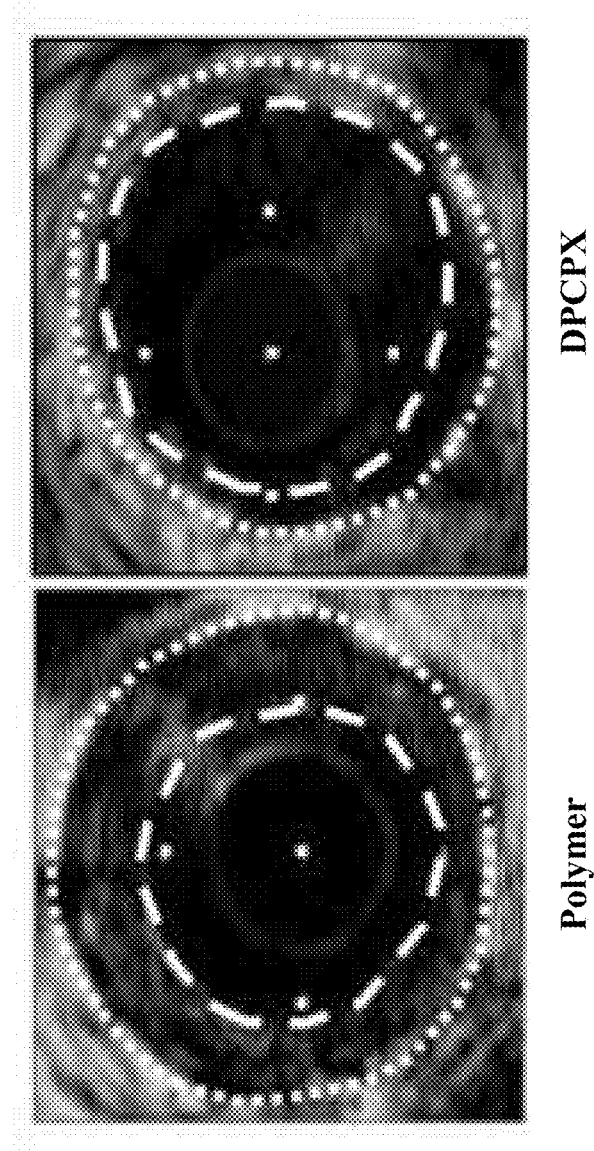

In-stent stenosis was quantified as the percent area covered with stenotic lesions in in-stent coronary segments in vivo using intravascular ultrasound (IVUS) right before sacrifice. Percent area in-stent stenosis=Area of Neointima/Area of Original Lumen indicated by stent struts×100. Adenosine $A_1R$ antagonist-eluting stents rivaled clinically used paclitaxel-eluting (Taxus®) stents in prevention of in-stent coronary stenosis in metabolic syndrome pigs (FIG. 6). Paclitaxel induced a 47% and 55% decrease in stenosis in metabolic syndrome pigs having stents deployed at 1.0 (FIG. 6A) and 1.3 (FIG. 6B) times lumen diameter, respectively. The decrease was comparable to the $A_1R$-selective antagonist DPCPX-induced 53% decrease in stenosis at 1.1 times lumen diameter (FIG. 6C). This result was measured by intravascular ultrasound (FIG. 6D), as well as angiography, and stereomicroscopy. There might be superior long-term benefit of $A_1R$ antagonist-eluting stents due to the selective action on coronary smooth muscle while having minimal effects on endothelium. On the other side of adenosine action the $A_{2B}$ receptor stimulates endothelial growth and nitric oxide release largely without affecting coronary smooth muscle cells. It is discovered that robust expression of adenosine $A_{2B}$ receptors is found in coronary endothelium. In-stent delivery of an adenosine $A_{2B}$ agonist is useful to facilitate growth of endothelial cells.

Paclitaxel, unlike adenosine receptor modulators, has non-selective cytotoxic on proliferating CSM and endothelium. In contrast, adenosine receptor modulators can selectively inhibit proliferation of CSM and/or facilitate endothelial cell growth.

Simultaneous targeted delivery of multiple adenosine receptor modulators, illustratively, a selective adenosine $A_1$ receptor antagonist, for example, DPCPX, and an $A_{2B}$ receptor agonist, for example, BAY 60-6583, via drug-eluting stents is efficacious for prevention of restenosis and late thrombosis.

Bare metal and paclitaxel stents were deployed in coronary arteries of lean and metabolic syndrome (MetS) pigs (n=5/group) with stent:artery ratios at 1.0 (A) and 1.3 (B), *p<0.01. Polymer-coated (Polymer, control) and DPCPX-eluting stents (DPCPX) were deployed concurrently in coronary arteries with stent:artery ratio of 1.1 in lean and MetS pigs (n=5/group, C), *p<0.01. (A-C) IVUS was done 4 weeks after stenting in vivo to evaluate in-stent stenosis. Percent area stenosis of in-stent segments was quantified by IVUS. FIG. 6D shows representative images of two in-stent coronary segments (Polymer vs. DPCPX) from the same MetS pig under angiography, IVUS. Images of the anterior descending artery were also captured under stereomicroscope. In-stent coronary segments were cut open after harvesting at sacrifice. Adventitia was outside stainless steel struts and neointima was inside.

Figure 7A:
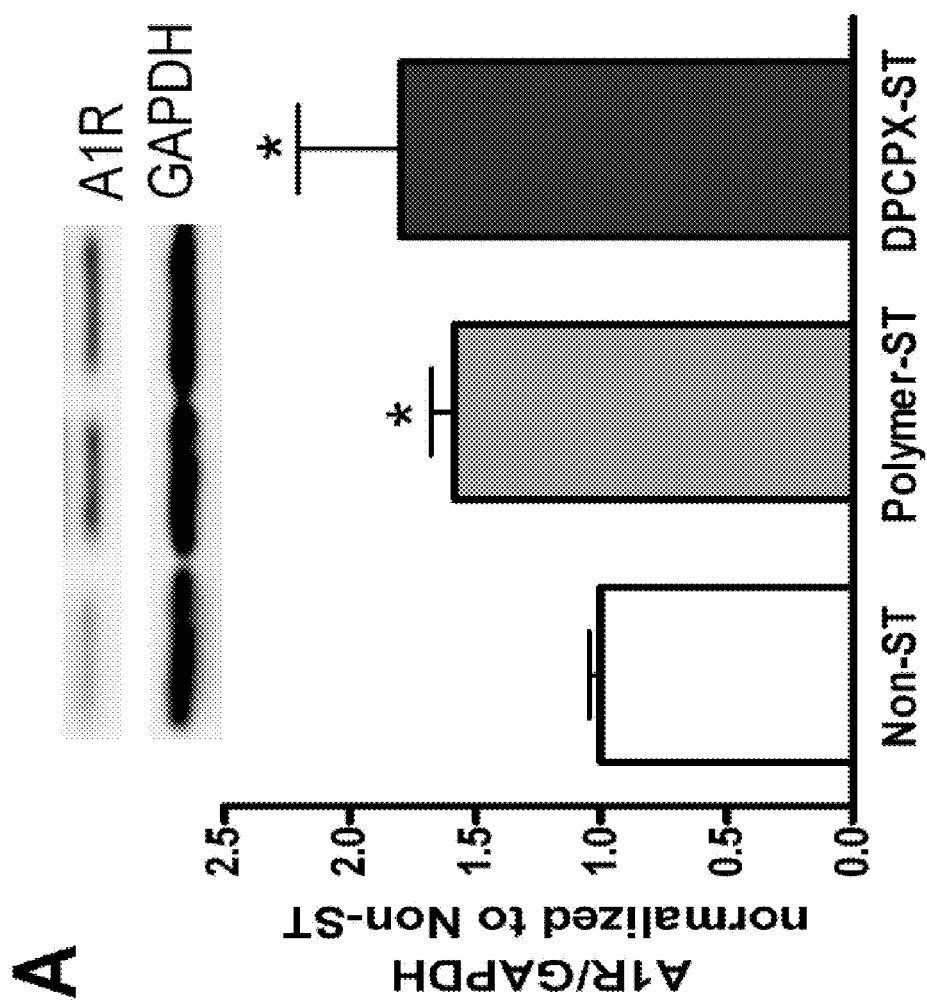
FIG. 7 shows $A_1R$ expression and $A_1R$-ERK1/2 signaling in polymer-coated stents and DPCPX-eluting stents. Coronary segments from lean pigs were treated with $A_1R$ selective agonist-CCPA ($10^{-6}$M) for 5 minutes and lysed for western blots. They were blotted for $A_1R$ (A), phospho- and total-ERK1/2 (B). Non-ST: nonstented right coronary segments; Polymer-/DPCPX-ST: coronary segments with the polymer/DPCPX coated stents implanted; * indicates statistical significance ($p<0.05$) when comparing to Non-ST; # indicates statistical significance ($p<0.05$) vs Polymer-ST.
Figure 7B:
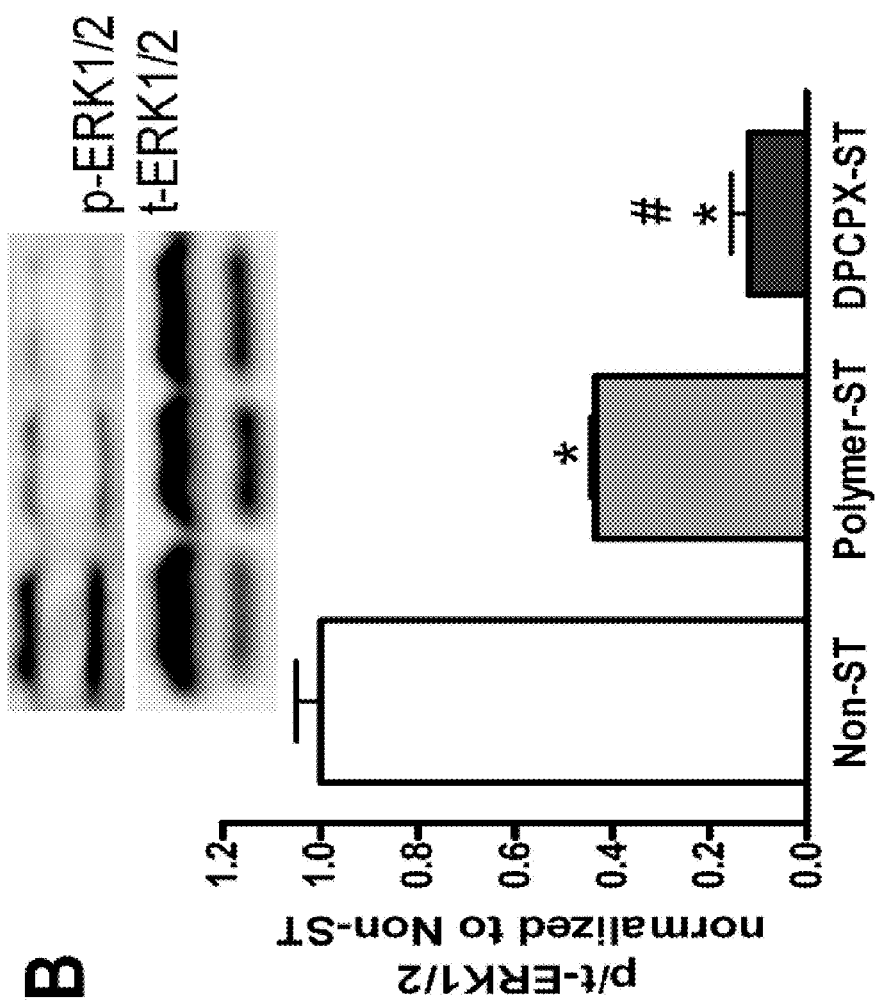

EXAMPLE. Coronary in-stent segments were treated with the $A_1R$-selective agonist CCPA for 5 minutes and then lysed and prepared for western blots (FIG. 7). $A_1R$, phosphorylated ERK1/2 (p-ERK1/2), and total ERK1/2 (t-ERK1/2) protein were determined by western blots. GAPDH protein served as loading control.

DPCPX-eluting stents reduced coronary ISS compared to polymer-coated stents in Ossabaw miniature swine. DPCPX-eluting stents with different drug dose densities and thicknesses were formulated for tailored drug-eluting profiles. The duration of drug release and release rates were efficiently modulated by adjusting the film thickness when the drug was uniformly distributed throughout the film. DPCPX eluted from a DES polymer was effective in reducing CSM proliferation by selective antagonism of the adenosine $A_1$ receptor. These studies demonstrate that adenosine receptors are a pertinent signaling pathway in restenosis and adenosine receptor modulators in DESs are useful to selectively inhibit CSM proliferation.

While the invention has been illustrated and described in detail in the foregoing description, such an illustration and description is to be considered as exemplary and not restrictive in character, it being understood that only the illustrative embodiments have been described and that all changes and modifications that come within the spirit of the invention are desired to be protected. Those of ordinary skill in the art may readily devise their own implementations that incorporate one or more of the features described herein, and thus fall within the spirit and scope of the present invention.

The following publications, and each additional publication cited herein, are incorporated herein by reference in their entirety.

(1) Khurana, R.; Martin, J. F.; Zachary, I. Gene therapy for cardiovascular disease: a case for cautious optimism. *Hypertension*, 2001, 38, 1210-1216.

(2) Nabel, E. G. Biology of the impaired endothelium. *Am. J. Cardiol.*, 1991, 68, 6C-8C.

(3) Edelman, E. R.; Rogers, C. Pathobiologic reponses to stenting. *Am. J. Cardiol.*, 1998, 81 (7A), 4E-6E.

(4) Ajani, A. E.; Waksman, R. Paclitaxel-eluting coronary stents. *New Engl. J. Med.*, 2004, 350 (20), 2099-2100.

(5) Ranade, S. V.; Miller, K. M.; Richard, R. E.; Chan, A. K.; Allen, M. J.; Helmus, M. N. Physical characterization of controlled release of paclitaxel from the TAXUS Express (2™) drug-eluting stent. *J. Biomed. Mater. Res., Part A* 2004, 71A (4), 625-634.

(6) Poon, M.; Marx, S. O.; Gallo, R.; Badimon, J. J.; Taubman, M. B.; Marks, A. R. Rapamycin inhibits vascular smooth muscle cell migration. *J. Clin. Invest.*, 1996, 98, 2277.

(7) Saia, F.; Lemos, P. A.; Hoye, A.; Sianos, G.; Arampatzis, C. A.; de Feyter, P. J.; van der Giessen, W. J.; Smits, P. C.; van Domburg, R. T.; Serruys, P. W. Clinical outcomes for Sirolimus—Eluting stent implantation and vascular brachytherapy for the treatment of in-stent restenosis. *Catheter. CardioVasc. InterVention*, 2004, 62 (3), 283-288.

(8) Sousa, J. E.; Costa, M. A.; Abizaid, A.; Abizaid, A. C.; Rensing, B. J.; Abizaid, A. S.; Tanajura, L. F.; Kozuma, K.; Langenhove, G. V.; Sousa, A. G. M. R.; Falotico, R.; Jaeger, J.; Popma, J. J.; Serruys, P. W. Sustained suppression of neointimal proliferation by sirolimus-eluting stents: One-year angiographic and intravascular ultrasound follow-up. *Circulation*, 2001, 104, 2007-2011.

(9) Chen, M.-C.; Liang, H.-F.; Chiu, Y.-L.; Chang, Y.; Wei, H.-J.; Sung, H.-W. A novel drug eluting stent spray-coated with multilayers of collagen and sirolimus. *J. Controlled Release*, 2005, 108, 178-189.

(10) Yan, S. F.; Harja, E.; Andrassy, M.; Fujita, T.; Schmidt, A. M. Protein kinase C beta/early growth response-1 pathway: a key player in ischemia, atherosclerosis, and restenosis. *J. Am. Coll. Cardiol.*, 2006, 48, A47-A55.

(11) Fetalvero, K. M.; Shyu, M.; Nomikos, A. P.; Chiu, Y. F.; Wagner, R. J.; Powell, R. J.; Hwa, J.; Martin, K. A. The prostacyclin receptor induces human vascular smooth muscle cell differentiation via the protein kinase A pathway. *Am. J. Physiol. Heart Circ. Physiol.*, 2006, 290, H1337-1346.

(12) Dénes, L.; Jednákovits, A.; Hargitai, J.; Pénzes, Z.; Balla, A.; Tálosi, L.; Krajcsi, P.; Csermely, P. Pharmacologically activated migration of aortic endothelial cells is mediated through p38 SAPK. *Br. J. Pharmacol.*, 2002, 136, 597-603.

(13) Jaconson, K. A.; Gao, Z.-G. Adenosine receptors as therapeutic targets. *Nature ReV. Drug Disc.*, 2006, 5, 247-264.

(14) Tawfik, H. E.; Teng, B.; Morrison, R. R.; Schnermann, J.; Mustafa, S. J. Role of A1 adenosine receptor in the regulation of coronary flow. *Am. J. Physiol.*, 2006, 291 (1), H467-H472.

(15) Edwards, J. M.; Alloosh, M. A.; Long, X. L.; Dick, G. M.; Lloyd, P. G.; Mokelke, E. A.; Sturek, M. Adenosin A1 receptors in neointimal hyperplasia and in-stent stenosis in Ossabaw miniature swine. *Coron. Artery Dis.*, 2008, 19, 27-31.

(16) Sturek, M.; Alloosh, M.; Wenzel, J.; Byrd, J. P.; Edwards, J. M.; Lloyd, P. G.; Tune, J. D.; March, K. L.; Miller, M. A.; Mokelke, E. A.; Brisbin, I. L., Jr. Ossabaw island miniature swine: cardiometabolic syndrome assessment. In *Swine in the Laboratory. Surgery, Anesthesia, Imaging, and Experimental Techniques*; Swindle, M. M., Ed.; CRC Press: Boca Raton, 2007; pp 397-402.

(17) Shen, J. Z.; Halenda, S. P.; Sturek, M.; Wilden, P. A. Novel mitogenic effect of adenosine on coronary artery smooth muscle cells: Role for the A1 adenosine receptor. *Circ. Res.*, 2005, 96 (9), 982-990.

(18) Feoktistov, I.; Goldstein, A. E.; Ryzhov, S.; Zeng, D.; Belardineli, L.; Voyno-Yasenetskaya, T.; Biaggioni, I. Differential expression of adenosine receptors in Human endothelial cells. Role of A2B receptors in angiogenic factor regulation. *Circ. Res.* 2002, 90, 531-538.

(19) Shen, J. Z.; Halenda, S. P.; Sturek, M.; Wilden, P. A. Cell-signaling evidence for adenosine stimulation of coronary smooth muscle proliferation via the A1 adenosine receptor. *Circ. Res.*, 2005, 97 (6), 574-582.

(20) Coates, J.; Sheehan, M. J.; Strong, P. 1,3,-Dipropyl-8-cyclopentyl Xanthine (DPCPX): a useful tool for pharmacologists and physiologist. *Gen. Pharmacol.*, 1994, 25, 387-394.

(21) Shim, J. O.; Shin, C. Y.; Lee, T. S.; Yang, S. J.; An, J. Y.; Song, H. J.; Kim, T. H.; Huh, I. H.; Sohn, U. D. Signal transduction mechanism via adenosine A1 receptor in the cat esophageal smooth muscle cells. *Cell. Signalling*, 2002, 14 (4), 365-372.

(22) Callegaria, A.; Bollinib, S.; Iopa, L.; Chiavegatoa, A.; Torregrossac, G.; Pozzobonb, M.; Gerosac, G.; De Coppib, P.; Elvassored, N.; Sartore, S, Neovascularization induced by porous collagen scaffold implanted on intact and cryoinjured rat hearts. *Biomaterials*, 2007, 28, 5449-5461.

(23) Holschbach, M. H.; Olsson, R. A.; Bier, D.; Wutz, W.; Sihver, W.; Schuller, M.; Palm, B.; Coenen, H. H. Synthesis and evaluation of no-carrier-added 8-cyclopentyl-3-(3-[F-18]fluoropropyl)-1-propylxanthine ([F-18]CPFPX): A potent and selective A(1)-adenosine receptor antagonist for in vivo imaging. *J. Med. Chem.*, 2002, 45 (23), 5150-5156.

(24) Yang, D.; Koupenova, M.; McCrann, D. J.; Kopeikina, K. J.; Kagan, H. M.; Schreiber, B. M.; Ravid, K. The A2b adenosine receptor protects against vascular injury. *Proc. Natl. Acad. Sci. U.S.A.*, 2008, 105, 792-796.

(25) Dubey, R. K.; Gillespie, D. G.; Shue, H.; Jackson, E. K. A2B receptors mediate antimitogenesis in vascular smooth muscle cells. *Hypertension*, 2000, 35, 267-272.

(26) Nakazawa, G.; Finn, A.; Virmani, R. Vascular pathology of drugeluting stents. *Herz*, 2007, 32, 274-280.

(27) Pan, C. J.; Tang, J. J.; Weng, Y. J.; Wang, J.; Huang, N. Preparation, characterization and anticoagulation of curcumin-eluting controlled biodegradable coating stents. *J. Controlled Release*, 2006, 116, 42-29.

(28) Sato A, Terata K, Miura H, Toyama K, Loberiza F R, Jr., Hatoum O A, Saito T, Sakuma I and Gutterman D D. Mechanism of vasodilation to adenosine in coronary arterioles from patients with heart disease. *Am J Physiol Heart Circ Physiol* 288: H1633-H1640, 2005.

(29) S. D. Shukla, et al., "Diabetic pig platelets exhibit hypersensitivity to thrombin," *Comp. Med.* 58, 481 (2008).

(30) H. A. Olanrewaju, et al., "Adenosine A(2A) and A(2B) receptors in cultured human and porcine coronary artery endothelial cells," *Am. J. Physiol. Heart Circ. Physiol.* 279(2), H650-H656 (2000).

(31) H. A. Olanrewaju and S. J. Mustafa, "Adenosine A2A and A2B receptors mediated nitric oxide production in coronary artery endothelial cells," *Gen. Pharmacol.* 35, 171 (2000).

(32) Raghvendra K. Dubey, Delbert G. Gillespie, and Edwin K. Jackson, "A2B Adenosine Receptors Stimulate Growth of Porcine and Rat Arterial Endothelial Cells," *Hypertension* 39(2), 530 (2002).

(33) Igor Feoktistov, et al., "Differential Expression of Adenosine Receptors in Human Endothelial Cells Role of A2B Receptors in Angiogenic Factor Regulation," *Circ. Res.* 90(5), 531 (2002).

(34) Tobias Eckle, et al., "Cardioprotection by Ecto-5'-Nucleotidase (CD73) and A2B Adenosine Receptors," 115(12), 1581 (2007).

(35) P. G. Baraldi, et al., "Recent improvements in the development of A(2B) adenosine receptor agonists," *Purinergic Signal.* 5, 3 (2009).

What is claimed is:

1. A device for implantation into a blood vessel, the device comprising a stent having a coating, where the coating consists of a biocompatible polymer that is poly(lactic-co-glycolic acid)-b-poly(L-lysinse) or polyurethane; 1,3-dipropyl-8-cyclopentyl xanthine (DPCPX); and optionally an adenosine $A_{2B}$ receptor agonist or an adenosine $A_{2A}$ receptor agonist,
wherein the DPCPX is released from the stent over a period of from about 7 days to about 100 days and the DPCPX has a surface density in the coating from 0.5 µg/mm² to 1 µg/mm².

2. The device of claim 1 wherein the coating consists of poly(lactic-co-glycolic acid)-b-poly(L-lysine) or polyurethane; DPCPX; and an adenosine $A_{2B}$ receptor agonist.

3. The device of claim 1 wherein the coating consists of poly(lactic-co-glycolic acid)-b-poly(L-lysine) or polyurethane; DPCPX; and an adenosine $A_{2A}$ receptor agonist.

4. A device for implantation into a blood vessel, the device consisting of a stent coated with a coating consisting of a biocompatible polymer and DPCPX,
wherein the DPCPX is released from the stent over a period of from about 7 days to about 100 days and the biocompatible polymer is selected from the group consisting of poly(lactic-co-glycolic acid)-b-poly(L-lysine), polyurethane, poly(styrene-b-isobutylene-b-styrene), or a combination thereof.

5. A method of treating restenosis in a patient, the method comprising the step of implanting the device of claim 1 into a blood vessel of the patient.

6. The device of claim 1 wherein the DPCPX is present at a ratio of 10 wt % (DPCPX:polymer).

7. The device of claim 1 wherein the DPCPX is present at a ratio of 20 wt % (DPCPX:polymer).

8. The device of claim 1 wherein the DPCPX is present at a ratio of 30 wt % (DPCPX:polymer).

9. The device of claim 1 wherein the surface density is 0.5 µg/mm² or 1 µg/mm².

10. The device of claim 1 wherein the surface density is 0.5 µg/mm².

11. The device of claim 1 wherein the coating has a thickness from about 5 µm to about 50 µm.

12. The device of claim 1 wherein the biocompatible polymer is poly(lactic-co-glycolic acid)-b-poly(L-lysine).

13. The device of claim 4 wherein the biocompatible polymer is polyurethane.

14. The device of claim 4 wherein the biocompatible polymer is poly(lactic-co-glycolic acid)-b-poly(L-lysine).

15. The device of claim 4 wherein the DPCPX has a surface density in the coating from 0.5 µg/mm² to 1 µg/mm².

16. The device of claim 4 wherein the DPCPX is present at a ratio of 10 wt % (DPCPX:polymer).

17. A device for implantation into a blood vessel, the device consisting of a stent coated with a coating consisting of a biocompatible polymer and DPCPX,
wherein the DPCPX is released from the stent over a period of from about 7 days to about 100 days, the biocompatible polymer is poly(lactic-co-glycolic acid)-b-poly(L-lysine), and the DPCPX has a surface density in the coating from 0.5 µg/mm² to 1 µg/mm².

18. The device of claim 17, wherein the surface density is 0.5 µg/mm² or 1 µg/mm², the coating has a thickness from about 5 µm to about 50 µm, the biocompatible polymer is poly(lactic-co-glycolic acid)-b-poly(L-lysine), and the DPCPX is present at a ratio of 10 wt % (DPCPX:polymer).

* * * * *